United States Patent [19]
Takazawa

[11] Patent Number: 5,965,430
[45] Date of Patent: Oct. 12, 1999

[54] BIOACTIVE SUBSTANCE HAVING ANTITUMOR ACTIVITY, PRODUCING STRAIN, AND PRODUCTION THEREOF

[75] Inventor: Hidenao Takazawa, Saitama, Japan

[73] Assignee: Senka Co., Ltd., Saitama, Japan

[21] Appl. No.: 08/923,691

[22] Filed: Sep. 4, 1997

[30] Foreign Application Priority Data

Sep. 4, 1996 [JP] Japan ...................... 8-255588

[51] Int. Cl.$^6$ ...................................... C12N 1/14
[52] U.S. Cl. ..................... 435/254.3; 435/915; 435/41; 424/195.1; 424/93.5
[58] Field of Search ................. 424/520, 195.1, 424/93.5; 435/254.3, 915, 41

*Primary Examiner*—Jean C. Witz
*Attorney, Agent, or Firm*—Young & Thompson

[57] ABSTRACT

Asn-linked glycoprotein having antitumor activity, with molecular weight of 32–84 kDa, its producing strain, production and use, adsorbs to Con. A. The process for its production comprises culturing a microorganism belonging to genus Aspergillus and isolating from the culture medium Asn-linked glycoprotein having a molecular weight of 32–84 kDa which adsorbs to Con. A, or a mixture thereof. The substance having antitumor activity is effective for treatment of solid tumors, ascites tumors, multiple cytoma and oval tumors and for the suppression of tumors.

15 Claims, 4 Drawing Sheets

SEPARATION OF CELL LYSATE BY
CON A-SEPHAROSE

1 : CELL LYSATES

2~4: PASSED FRACTIONS WITH VARIOUS
CHARGINGS (CF: EXPERIMENTAL
METHOD)

4~7: ELUTED FRACTIONS WITH VARIOUS
CHARGINGS (CF: EXPERIMENTAL
METHOD)

SEPARATION OF CELL LYSATE BY
CON A-SEPHAROSE

1 : CELL LYSATES

2~4: PASSED FRACTIONS WITH VARIOUS
   CHARGINGS (CF: EXPERIMENTAL
   METHOD)

4~7: ELUTED FRACTIONS WITH VARIOUS
   CHARGINGS (CF: EXPERIMENTAL
   METHOD)

BIOACTIVE SUBSTANCE HAVING ANTITUMOR ACTIVITY, PRODUCING STRAIN, AND PRODUCTION THEREOF

FIELD OF THE INVENTION

This invention relates to Asn-linked glycoproteins having antitumor activity and molecular weights of 32–84 kDa, a mixture thereof, their producing microorganism, and the production thereof.

PRIOR ART

Fungi Aspergillus have been known for use as food additives to Miso and soysauce (Pathogenic Mycology, p. 78–80, 1987, Nanzando Publ., Tokyo) and are known to have bactericidal activities (White, E. C. et al. J. Bacteriol. 45: p. 433–422, 1942). Studies on application of these activities seemed, however, to be few (Dutcher, J. G. J. Biol. Chem. 171: 321–339, 1947).

PROBLEMS TO BE SOLVED BY THE INVENTION

We have tried to study the activities of Aspergillus and have examined its actions on cancer cells and gingival cells.

We have concentrated on the physiological activities of plant compositions on human and animals, and hypothesized that parasitic microorganisms of plants might have such activities. Accordingly, we have tried to isolate various microorganisms from plants and in the course of doing so have completed the present invention.

SUMMARY OF THE INVENTION

The present invention relates to a bioactive substance having antitumor activity, producing microorganism, production and use thereof. The present invention relates, therefore, to Asn-linked glycoproteins having molecular weights of 32–84 kDa and adsorbing to Con. A, or mixtures thereof.

According to the embodiments of the present invention, the glycoproteins or mixtures thereof are Aspergillus-derived substances, and the microorganism is *Aspergillus Flavus* strain SRT.

According to another embodiment of the present invention, the invention relates to a microorganism belonging to genus Aspergillus which produces Asn-linked glycoproteins having molecular weights of 32–84 kDa.

According to another embodiment of the present invention, the invention relates to a process for production of Asn-linked glycoproteins having molecular weights of 32–84 kDa, which adsorb to Con. A, comprising culturing a microorganism belonging to genus Aspergillus which produces Asn-linked glycoproteins having molecular weights of 32–84 kDa, which adsorb to Con. A, and isolating the Asn-linked glycoprotein thus produced.

According to still another embodiment of the present invention, the invention relates to the antitumor active agent used for the treatment of solid tumor, ascites tumor, polymorphocellular sarcoma, the suppression of metastasis of tumors, or the treatment of intraoral tumors.

DETAILED DESCRIPTION OF THE PREFERRED EMBODIMENTS

Figure 1:
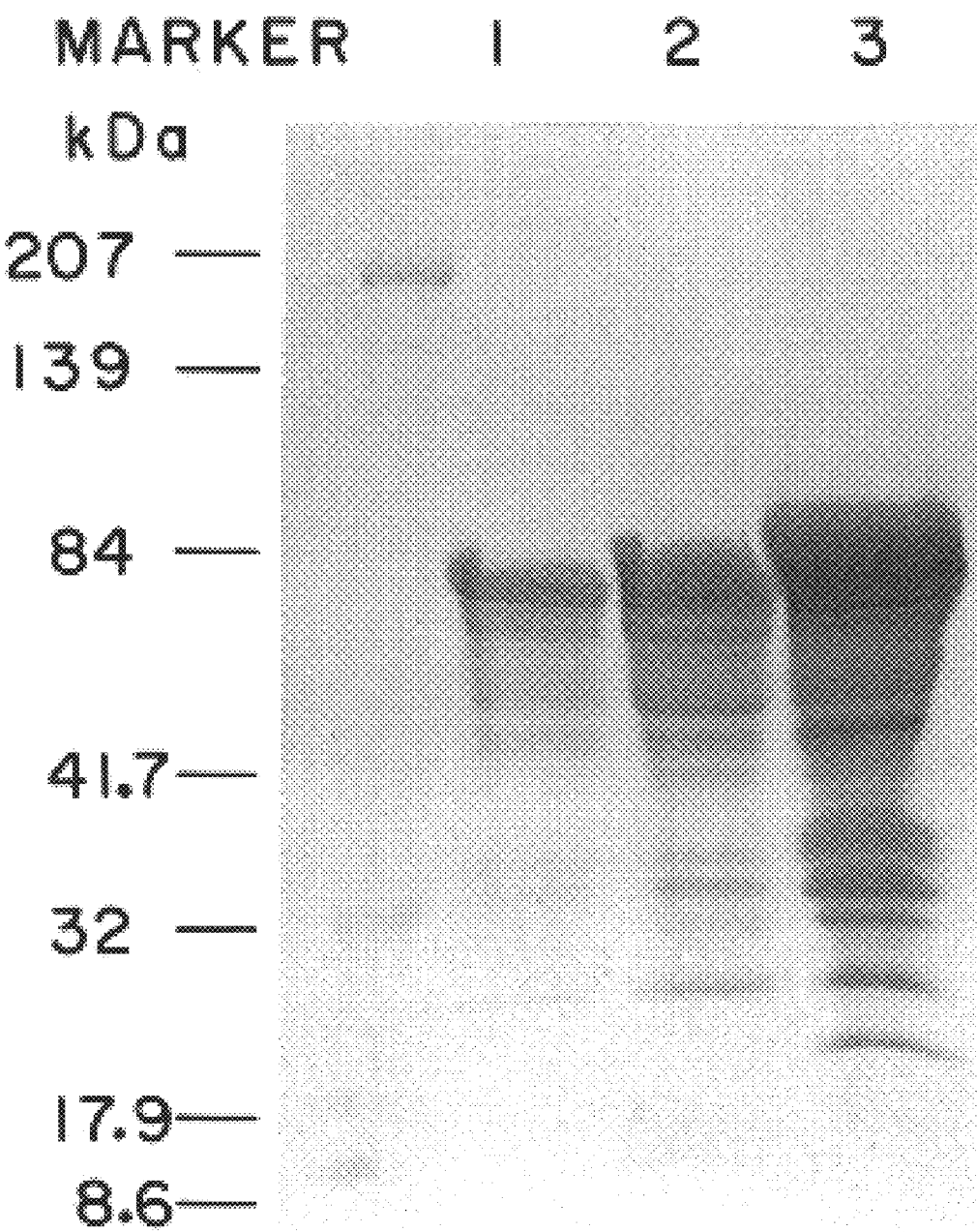
FIG. 1: CBS stain of the substance.

We have tried to isolate microorganisms from plants by means of the following procedures.

1. Various plants, for example, grasses, trees, crops or seeds are washed with tap-water, twice washed with re-distilled water, and dried in the air in the room for overnight.

2. Dried plants are collected in a group.

3. The plants are physically crushed using homogenizer (glass-made, 20 ml, Iwaki Glass Works, Japan) or a mortar (porcelain, 120 mm φ, Tokyo Glass Works, Japan). Before crushing, the plant stems and roots are cut.

4. Crushed plants are suspended in re-distilled water.

5. Concentration and volume of the suspension in the test tubes are adjusted to equal levels.

6. The contaminated bacteria in the suspensions are sterilized at 121° C. for 15 minutes using autoclave (Type HA-240 MII, Hirayama Seisakusho, Japan).

7. The supernatant obtained from the above is spread with 0.8 ml/plate on the commercially available 5 potato dextrose agar plates containing chloramphenicol 25 mg/l (90 mm φ, Kojin Bio Inc., Japan), and incubated at 37° C. (incubater Type 1H42/42M, Yamato Sci. Inc., Tokyo), after rocking the plates.

8. Colonies are observed after 10 days.

9. Colonies at diameter 8–15 mm are collected using 5 ml screw tube bottle (Laboran, lot. No. 9-852-04, Seieido Inc., Japan).

10. Separated microorganisms are stored in the freezer below −20° C. (EV200N x K, Whirlpool, USA), and can also be stored at room temperature (20–25°C.) for 1–2 years.

Microorganism having producing activities of the substance of the present invention belongs to genus Aspergillus. Preferable strain is *Aspergillus flavus* which was isolated from the plants by us. Taxonomical properties are shown in the following. Example of the strain is *Aspergillus Flavus* STR.

I. The strain shows good growth on potato dextrose agar. Czapek agar and malt extract agar. and conidia are abundantly attached. Observation on the colonies grown on potate dextrose agar shows that Deuteromycotina is formed on the whole of the vesicles, with metulae 13–16×4–4.8 μm, phialide 7–9.5 ×2–2.4 μm and diameter of conidia 2.4–3.2 μm with spherical to oval and rough to warty walls.

II. Properties on the cultured medium (1) Culture properties of the strain of the present invention are shown in Table 1. Results are shown with macroscopical observation after 10 days culture on various media at 25° C.

TABLE 1

| Medium | Growth (Diameter of colony, mm) | Color of colony surface | Color of colony reverse | Soluble pigment |
|---|---|---|---|---|
| Potate dextrose agar | Good, Cottony grown, Conidia, slightly dense attaching | Yellowish-green | Pale yellowish white | None |
| Czapek agar | Good, Cottony growth, Conidia, slightly dense attaching | Yellowish-green | Pale yellow | None |
| Malt extract agar | Good, Cottony growth, Conidia, slightly dense attaching | Yellowish-green | Pale yellow | None |

(2) Growth conditions on potato dextrose agar at 37° C. for 15 days were good growth (>15 mm ). No growth was observed at 4° C. for 15 days.

III Physiological properties
(1) Growth temperature: 25–38° C.
(2) Optimum growth temperature: 36.5–37° C.
(3) Growth pH: 5.4–7.5
(4) Optimum pH: 6.7–7.2
(5) Aerobic nature: aerobic Based on the above taxonomical properties, the strain is consulted with Illustrated Fungi, Vol. 2 (1991, Kodansha Publ. Tokyo ), and is referred to belong genus Aspergillus and is designated as *Aspergillus Flavus* SRT. The strain was deposited in National Institute of Bioscience and Human Technology Agency of Industrial Science and Technology of 1–3, Higashi 1 chome Tsukuba-shi, Ibarakiken on Mar. 3th, 1995 and was given permanent accession No. FERM BP-5030.

*Aspergillus Flavus* , preferably *Aspergillus Flavus* SRT (FERM BP-5030) is cultrued in the medium for obtaining the substance of the present invention. Conventional medium for fungi is used. Submerged aeration culture is preferable used in an industrial culture. Culturing temperature is applied for suitable temperature used in the culture of fungi, i.e. at 18–37° C., preferably at 20–28° C. Culturing time is a suitable time for growth of fungal mycelia and is usually for 5–15 days, preferably 7–12 days. After cultivation, mycelia are separated such as by centrifugation and filter press.

In the separation of cells, filter aid, for example diatomaceous earth (Celite etc.) is added. if necessary. Separated cells are, lysed by a method used for mycelial lysis, for example combination of cell wall lysis by enzyme and detergents. Enzyme such as Novozyme 234 (Wako Pure Chemical Works, Japan) is used at 30° C. for 2 hours. Effective lysis of mycelial cells is performed by treatment of detergents such as sodiumdodecyl sulfate after enzyme treatment.

Composition of cell lysates was examined by protein analysis and PAS (periodic acid Schiff) stain (hereinafter designates as PAS stain), and glycoprotein is determined by SDS-PAGE (SDS-polyacrylamide gel electrophoresis).

[A] Electrophoresis
(1) Gel: 4–20% a SDS-PAGE mini-gel (TEFCO, USA).
(2) Staining: CBB (Coomassie BrilliantBlue) stain (hereinafter designates as CBB stain) and PAS stain.
(3) Electrophoresed samples are shown in Table 2.

TABLE 2

| No. | Sample | Charged volume |
| --- | --- | --- |
| 1 | cell lysates | 10 µl |
| 2 | cell lysates | 20 µl |
| 3 | cell lysates | 50 µl |

In Table 2, electrophoresis could not be performed because of large volume of sample No. 3. Accordingly trichloroacetic acid (hereinafter designates as TCA) precipitated protein was supsended in 0.1 N NaOH 20 µl and electrophoresed.

[B] Molecular weight

Molecular weight of the protein was estimated using image analysis (AE6900M,ATTO Inc., Japan) comparing with molecular weight markers which were electrophoresed simultaneously. CBB stain of the electrophoresis is shown in FIG. 1. Approximately 20–84 kDa protein bands were observed. PAS stain of the bands resulted major 3 bands of proteins [a: estimated molecular weight; 63.8 kDa (a=65±7 kDa), b: estimated molecular weight; 59.7 kDa (b=58±6 kDa) and c: estimated molecular weight; 49.0 kDa (c=48±5 kDa)].

[C] Isolation of glycoprotein

Cell lysis was fractionated using lectin column (5 cm×ϕ01.5 cm, Seikagaku Kogyo Inc., Japan), which adsorb specifically glycoprotein and analysed by SDS-PAGE.

(1) Experimental: Separation of glycoprotein by lectin column
① Column: Concanavalin A (Con. A)-Agarose and caster lectin (RCA)-Agarose
② Isolation process:

---

Equilibrium of column by buffer solution*
↓
Adsorption of cell lysis on column
↓
Fractionation of unadsorbed protein (passed fractions)
↓
Collection of adsorbed fractions and elution by an eluate** (eluted fractions)

*Con. A-Agarose:
50 mM Tris-HCl (pH 7.2), 0.1M NaCl, 1 mM $MgCl_2$, 1 mM $CaCl_2$
RCA-Agarose: 0.1M K—$PO_4$ (pH 7.2), 0.15M NaCl
**eluate:
Con. A-Agarose: buffer containing 0.2M methyl-α-D-mannoside
RCA-Agarose: buffer containing 0.2M galactose

[D] Electrophoresis
(1) Gel: 4–20% SDS-PAGE mini-gel (TEFCO, USA)
(2) Staining: CBB stain and PAS stain
(3) Electrophresed samples are shown in Table 3.

TABLE 3

| No. | Sample | Charged amount | Note |
| --- | --- | --- | --- |
| 1 | cell lysates (pre-fraction) | 15 µl | — |
| 2 | Passed fraction | 50 µl | TCA precipitation* |
| 3 | Passed fraction | 100 µl | TCA precipitation* |
| 4 | Passed fraction | 150 µl | TCA precipitation* |
| 5 | Eluted fraction | 100 µl | TCA precipitation* |
| 6 | Eluted fraction | 200 µl | TCA precipitation* |
| 7 | Eluted fraction | 500 µl | TCA precipitation* |

Figure 3:
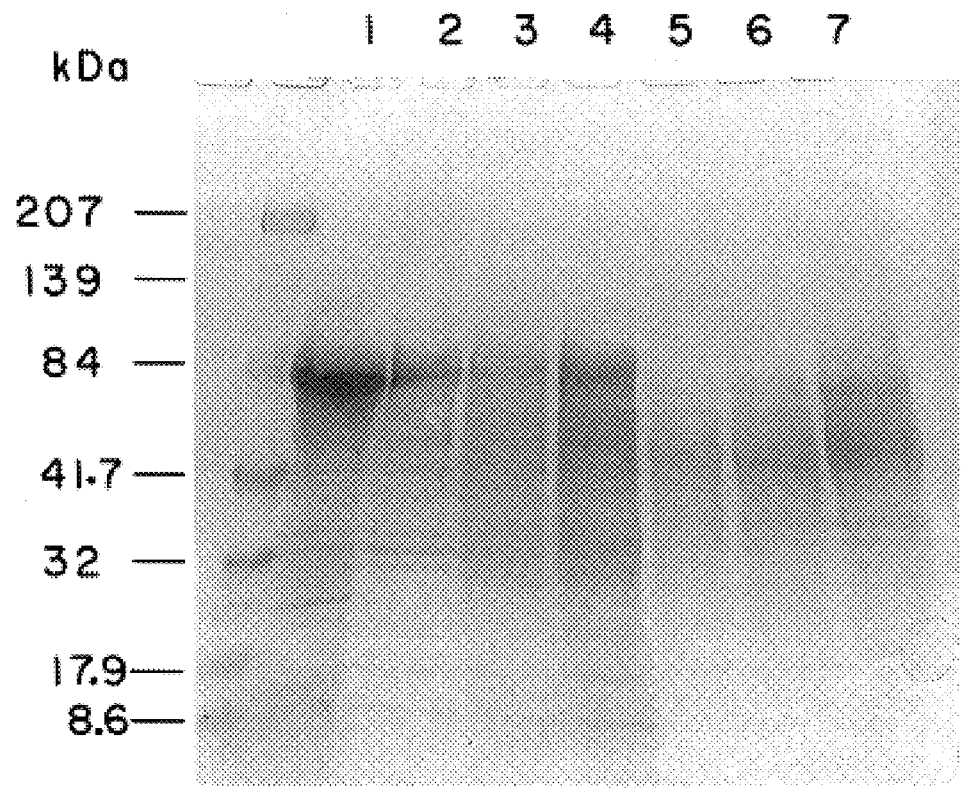
FIG. 3: Separation of the substance of Con. A-Sepharose.
Figure 4:
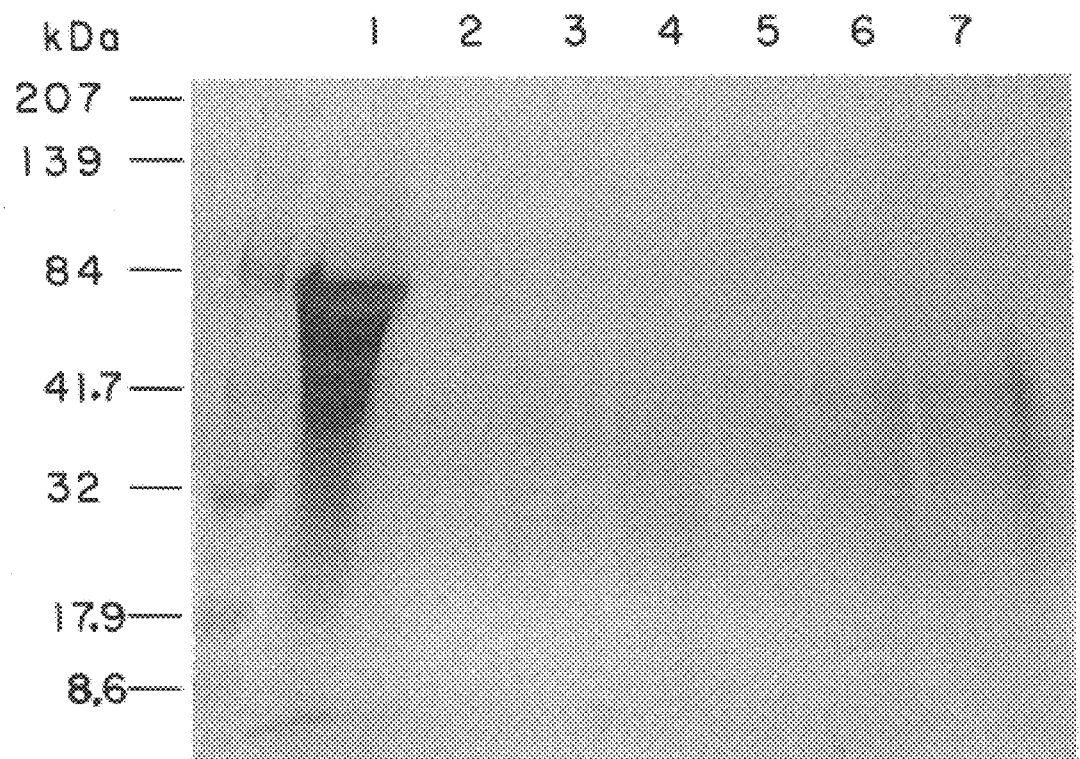
FIG. 4: PAS stain of the substance by Con. A-Sepharose.

*TCA (Trichloroacetic acid) precipitation method:
Sample
↓ ← 1/10 vol. 0.15% sodium deoxycholate
room temp., 10 min.
↓ ← 1/10 vol. 72% TCA
4000 × g, 20 min. centrifuge
↓
Precipitation, 20 µl 0.1N—NaOH suspension Con. A and RCA of the lectins are used in this invention. Con. A binds with polymannose type and complex type side chains of the sugar chains, which have more than two α-mannose residues of unsubstituted C-3, 3, 6-hydroxyls in asparagine (Asn)-linked glycoprotein, RCA has strong affinity for N-acetylglucosamine (Gal β1-4GlcNAc) in asparagine (Asn)-sugar chain and mucin sugar chain Gal β-3GalNAc. No adsorbed protein in RCA-Sepharose was found. Some protein are adsorbed in the Con. A-Sepharose column (FIG. 3). PAS stain is shown in FIG. 4. As a result, Asn-linked glycoprotein Result of which absorbed in Con. A column is found in cell lysates.

Most preferable microorganism in this invention is *Aspergillus Flavus* SRT (FERM BP-5030). However microorganisms are easily mutated, therefore natural and artificial mutants of *Aspergillus Flavus* SRT (FERM BP-5030) as well as the strains belonging to *Aspergillus Flavus* which can produce the compound of the present invention are all involved in the present invention.

EMBODIMENTS OF THE INVENTION

Following examples illustrate the present invention, but are not construed as limiting.

EXAMPLE 1

One loopful *Aspergillus Flavus* SRT (FERM BP-5030) was inoculated in liquid medium 100 ml in 500 ml Sakaguchi flask and shake cultured at 27° C. for 10 days. The cultured broth was inoculated into liquid medium 10 lit. in 30 lit. jar-fermenter and cultured at 27° C. for 10 days under aeration 1 lit./min. with stirring at 150–200 rpm. Cells were separated by centrifugation to obtain wet cells 1 g. Novozyme 234 (Wako Pure Chem. Co., Japan) 0.5 mg/10 mg of dry cells were added to the cells and treated at 30° C. for 2 hours. Treated cells were washed with 50 mM phosphate buffer solution pH 7.2 and the cells were lysed with 1% SDS. The mycelial lysate was centrifuged at 10×g for 20 minutes. Supernatant was lyophilized to obtain lyophilyzate 1 mg.

The lyophilyzate was dissolved in a small amount of 50 mM phosphate buffer pH 2.2 and electrophoresed by SDS-PAGE to determine protein compositions. Glycoprotein was detected by PAS stain. Conditions of electro-phoresisis are shown below and SDS-PAGE was performed by the conventional method.
(1) Gel: 4–20% SDS-PAGE mini-gel (TEFCO, USA)
(2) Staining: CBB stain and PAS stain
(3) Electrophresed samples are shown in Table 4.

TABLE 4

| No. | Sample | Charged amount |
|---|---|---|
| 1 | solution of lyophilizate | 10 μl |
| 2 | solution of lyophilizate | 20 μl |
| 3 | solution of lyophilizate | 50 μl |

In Table 4, electrophoresis could not be performed because of large volume of sample No. 3. Accordingly trichloroacetic acid (hereinafter designates as TCA) precipitated protein was suspended in 0.1 N NaOH 20 μl and electrophoresed.

```
Sample 50 μl
  ↓ ← 5 μl 0.15% sodium deoxycholate
  ↓ room temperature 10 min.
  ↓ ← 5 μl 72% TCA
  ↓ 4000 × g, 20 min. centrifuge
precipitation, dissolved with 20 μl 0.1N NaOH suspension
```

Figure 2:
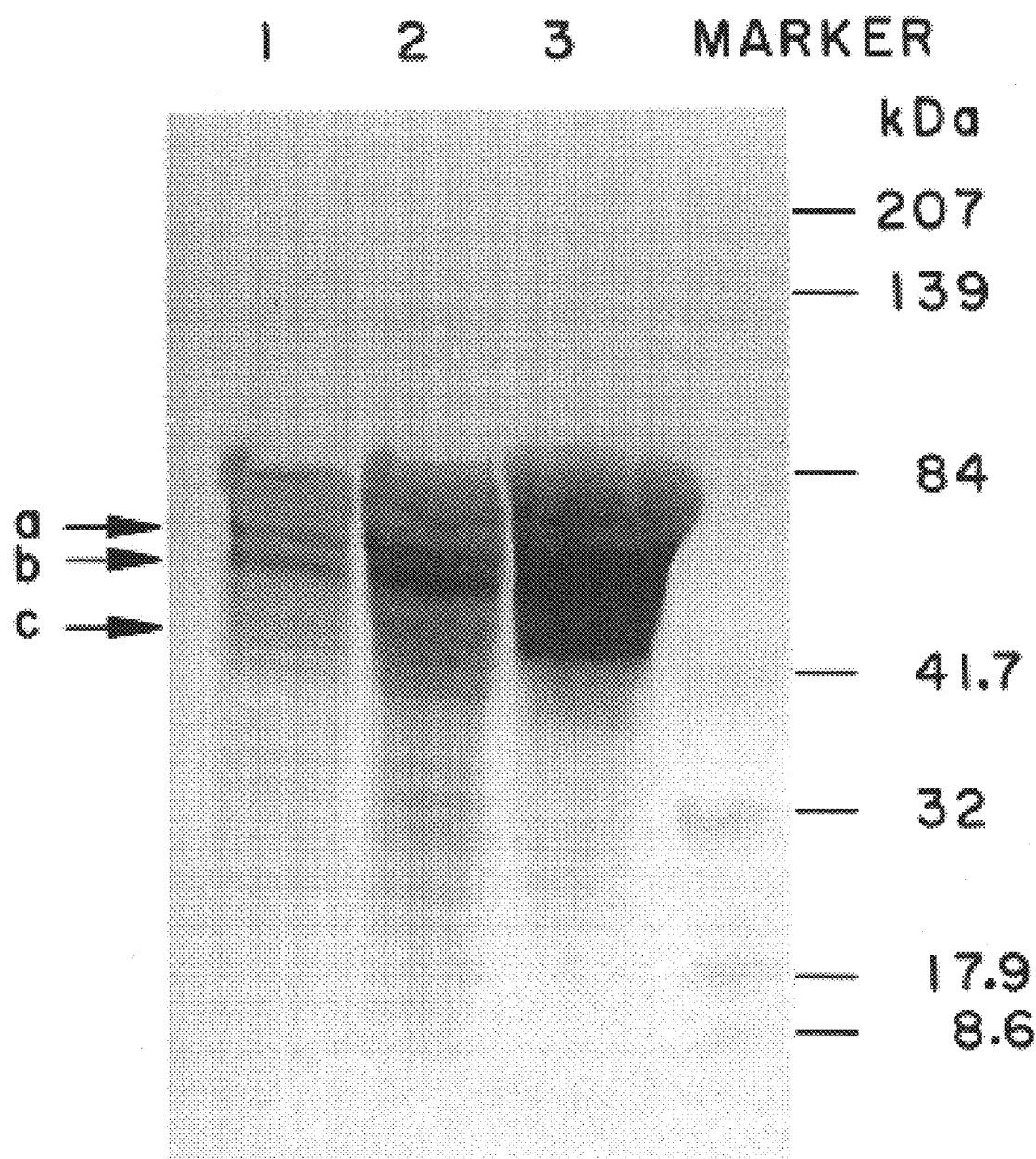
FIG. 2: PAS stain of the substance.

Molecular weight of the protein was estimated using image analysis comparing with molecular weight markers which were electrophoresed simultaneously. CBB stain of the electrophoresis is shown in FIG. 1. Approximately 20–84 kDa protein bands were observed. PAS stain of the bands (FIG. 2) resulted major 3 bands of proteins [a: estimated molecular weight; 63.8 kDa (a=65±7 kDa), b: estimated molecular weight: 59.7 kDa (b=58±6 kDa) and c: estimated molecular weight; 49.0 kDa (c=48±5 kDa)].

The major bands were shown high C DB staining and were estimated as glycoprotein.

EXAMPLE 2

Lyophilized powder 1 mg obtained in Example 1 was dissolved in 50 mM phosphate buffer, pH 7.2, 50 ml. The solution was fractionated using lectin column (length 5 cm×diameter 1.5 cm, Seikagaku Kogyo Inc. Japan) and analysed by SDS-PAGE (TEFCO, USA).
1. Separation of glycoprotein by lectin column
   (1) Column: Concanavalin A (Con. A)-Agarose and caster lectin (RCA)-Agarose (2) Isolation process:

Equilibrium of column by buffer solution*
↓
Adsorption of lyophilized powder solution obtained in Example 1
↓
Fractionation of unadsorbed protein (passed fractions)
↓
Collection of adsorbed fractions and elution by an eluate** (eluted fractions)
The obtained fractions were lyophilized to obtain lyophilizate; a: 0.2 mg, b: 0.1 mg, and c: 0.1 mg.

*buffer solution:
Con. A-Agarose: 50 mM Tris-HCl (pH 7.2), 0.1M NaCl, 1 mM MgCl$_2$, 1 mM CaCl$_2$
RCA-Agarose: 0.1M K—PO$_4$ (pH 7.2), 0.15M NaCl
**eluate:
Con. A-Agarose: buffer containing 0.2M methyl-α-D-mannoside
RCA-Agarose: buffer containing 0.2M galactose 2. Electrophoresis
   (1) Gel: 4–20% SDS-PAGE mini-gel (TEFCO, USA)
   (2) Staining: CBB stain and PAS stain
   (3) Electrophresed samples are shown in Table 5.

TABLE 5

| No. | Sample | Charged amount | Note |
|---|---|---|---|
| 1 | Solution of lyophilized cell lysates (pre-fractionation) | 15 μl | |
| 2 | Passed fractionation | 50 μl | TCA precipitated protein was suspended in 20 μl 0.1N NaOH and electrophoresed |
| 3 | Passed fractionation | 100 μl | TCA precipitated protein was suspended in 20 μl 0.1N NaOH and electrophoresed |
| 4 | Passed fractionation | 150 μl | TCA precipitated protein was suspended in 20 μl 0.1N NaOH and electrophoresed |
| 5 | Eluted fractionation | 100 μl | TCA precipitated protein was suspended in 20 μl 0.1N NaOH and electrophoresed |
| 6 | Eluted fractionation | 200 μl | TCA precipitated protein was suspended in 20 μl 0.1N NaOH and electrophoresed |
| 7 | Eluted fractionation | 500 μl | TCA precipitated protein was suspended in 20 μl 0.1N NaOH and electrophoresed |

TCA precipitation was performed as follows.

```
Sample 50 μl
  ↓ ← 1/10 vol. 0.15% sodium deoxycholate
  ↓ room temperature 10 min.
  ↓ ← 1/10 vol. 72% TCA
  ↓ 4000 × g, 20 min. centrifuge
precipitation, dissolved with 20 μl 0.1N NaOH suspension
```

Con. A and RCA of the lectins were used in this invention. Con. A binds with polymannose type and complex type side chains of the sugar chains, which have more than two α-mannose residues of unsubstituted C-3, 3. 6-hydroxyls in asparagine (Asn)-linked glycoprotein. RCA has strong affinity for N-acetylglucosamine (Gal β1-4GlcNAc) in asparagine (Asn)-sugar chain and mucin sugar chain Gal β-3GalNAc. No adsorbed protein in RCA-Agarose was found. Some protein were adsorbed in the Con. A -Agarose column and staining by PAS stain was also observed. As a result, Asn-linked glycoprotein which adsorbed in Con. A column is found in cell lysates.

EXAMPLE 3

Antitumor Activity and Safety Tests

Sarcoma-180 was inoculated in subcutaneously or intraperitoneally in mice and the substance of the present invention was administered to determine life prolongation effect and suppression of tumor growth. 60 mice, STD:DDY, male, 4 weeks old, SLC Inc., Japan were acclimatized for 2 weeks and provided experiment at 6 weeks old. Dose and administration were performed by the following methods.

a) Lyophilized powder 1 mg obtained in Example 1 was dissolved in physiological saline 10 ml. 0.1 ml of the solution was subjected to 2-fold dilution and administered (0.2 ml/mouse) intraperitoneally every other days. Control was administered physiological saline (0.2 ml/mouse) i.p. every other days (ascites tumor mice).

b) 10 μl of the above solution were administered in the center of solid tumor in every other days using micro syringe (MS-N 100, Itoh Seisakusho Inc., Japan). Same volume of physiological saline was administered as a control (solid tumor mice). Substance of the present invention was started to administer in day 2 after inoculation of tumor (5 times administered 5 group) and day 4 (4 times administered group).

Sarcoma-180 was used. Tumor cells $5 \times 10^8/0.2$ ml was administered i.p. for ascites tumor type. Weight of ascites tumor was determined by that ascites tumor was adsorbed in dry cotton and reduced from body weight. Solid tumor weight was determined by that right lower limbs combined with tumor were amputated at the inguinal region and the weight thereof was reduced from mean of the weight of left lower limbs.

Type of tumor, terms for administration after transplantation of the tumor and administration routes were defined as follows.

A) Ascites tumor (administered on and from day 2 after tumor inoculation, administered every other days for 5 times)

1) Ascites control (physiological saline, i.p. 0.2 ml/mouse, n=5)

2) Ascites experimental (substance, i.p. 0.2 ml/mouse, n=6)

B) Solid tumor (administered on and from day 2 after tumor inoculation, administered every other days for 5 times)

3) Solid control (physiological saline, 10 gl/mouse, n=5)

4) Experimental (substance administered, in tumor; 10 μl/mouse, n=6)

5) Experimental (substance administered, i.p., 0.2 ml/mouse, n=6)

C) Solid tumor (administered on and from day 4 after tumor inoculation, administered every other days for 5 times)

6) Experimental (substance administered, i.p./in tumor, 0.2 ml/mouse and 10 μl/mouse, respectively, n=6)

D) Safety test (substance, administered in normal healthy mice, every other days for 10 times)

7) Safety test (substance, i.p., 0.2 ml/mouse, n=6)

E) Control (physiological saline, administered in normal healthy mice, every other days for 5 times or 10 times)

8) Control (physiological saline, administered every other days, 5 times, i.p., 0.2 ml/mouse, n=6)

9) Control (physiological saline, administered every other days, 10 times, i.p., 0.2 ml/mouse, n=5)

Results

Antitumor Effect of the Substance Obtained in Example 1 for Sarcoma-180

Body weights of Sarcoma-180 inoculated i. p. mice were all increased after 4 days of inoculation. Significant differences of the increased body weight in ascites control group (day 4, p<0.01) and substance administered ascites group (day 5, p<0.01) compared to the normal control group (non tumor bearing group) were observed. Body weight of the substance i.p. administered group (ascites tumor group) seemed to be suppressed after 2nd administration (after 4 days of tumor inoculation). Results are shown in Table 6.

TABLE 6

| | Days after tumor implantation | | | | | |
|---|---|---|---|---|---|---|
| | 0 | 2 | 4 | 6 | 8 | 10 |
| Control (physiological saline, i.p. n = 6) | | | | | | |
| Mean | 30.8 | 31.4 | 32.0 | 32.4 | 34.8 | 34.6 |
| (S.E.) g | (0.34) | (0.38) | (0.38) | (0.45) | (0.45) | (0.49) |
| Control, ascites (physiological saline, i.p. n = 5) | | | | | | |
| Mean | 30.1 | 30.5 | 34.1** | 37.5** | 39.9** | 39.5** |
| (S.E.) g | (0.41) | (0.48) | (0.95) | (1.20) | (1.59) | (1.91) |
| Substance administered group, ascites (i.p. n = 6) | | | | | | |
| Mean | 30.5 | 31.7 | 35.5 | 35.7** | 38.8*** | 39.3 |
| (S.E.) g | (0.59) | (0.73) | (0.84) | (0.93) | (0.53) | (2.19) |

Substance of the present invention administered group: Administration of the substance initiated after 2 days implantation of tumor cells intraperitoneally. Significant difference for the control group : p < 0.01, *: p < 0.001.
S.E.: Standard error.

Body weight of the substance administered group (solid tumor group) seemed to increase compared to normal healthy control group after 6 days of tumor inoculation. No body weight difference was observed among the tumor inoculated groups. Results are shown in Table 7.

TABLE 7

| | Days after tumor implantation | | | | | |
|---|---|---|---|---|---|---|
| | 0 | 2 | 4 | 6 | 8 | 10 |
| Control (physiological saline, i.p. n = 6) | | | | | | |
| Mean | 30.8 | 31.4 | 32.0 | 32.4 | 34.8 | 34.6 |
| (S.E.) g | (0.34) | (0.38) | (0.38) | (0.45) | (0.45) | (0.49) |
| Control, Solid tumor (physiological saline, administered in tumor, n = 5) | | | | | | |
| Mean | 30.2 | 30.6 | 32.2 | 33.7 | 36.0 | 36.2 |
| (S.E.) g | (0.51) | (0.42) | (0.44) | (0.57) | (0.62) | (0.77) |
| Substance administered group, solid tumor (administered in tumor, n = 6) | | | | | | |
| Mean | 31.8 | 31.8 | 33.3 | 34.7 | 36.8* | 36.6 |
| (S.E.) g | (0.36) | (0.42) | (0.67) | (0.71) | (0.77) | (0.98) |
| Substance administered group, solid tumor (i.p. administration, n = 6) | | | | | | |
| Mean | 30.9 | 31.1 | 31.7 | 33.2 | 36.4 | 36.1 |
| (S.E.) g | (0.56) | (0.55) | (0.61) | (0.67) | (0.82) | (0.87) |

Substance of the present invention administered group: Administration of the substance initiated after 2 days of implantation of tumor cells intraperitoneally or in the solid tumor.
Significant difference for the control group **: p < 0.05.
S.E.: Standard error The same tendency was observed in the substance administered groups after 4 days of tumor inoculation. Results are shown in Table 8.

TABLE 8

| | \multicolumn{6}{c}{Days after tumor implantation} | | | | | |
|---|---|---|---|---|---|---|
| | 0 | 2 | 4 | 6 | 8 | 10 |
| \multicolumn{7}{c}{Control (physiological saline, i.p. n = 6)} | | | | | | |
| Mean | 30.8 | 31.4 | 32.0 | 32.4 | 34.8 | 34.6 |
| (S.E.) g | (0.34) | (0.38) | (0.38) | (0.45) | (0.45) | (0.49) |
| \multicolumn{7}{c}{Control, solid tumor (physiological saline, administered in tumor, n = 5)} | | | | | | |
| Mean | 30.2 | 30.6 | 32.2 | 33.7 | 36.0 | 36.2 |
| (S.E.) g | (0.51) | (0.42) | (0.44) | (0.57) | (0.62) | (0.77) |
| \multicolumn{7}{c}{Substance administered group (administered in the tumor or i.p. n = 6)} | | | | | | |
| Mean | 30.8 | 31.6 | 33.7* | 34.7** | 35.6 | 36.3 |
| (S.E.) g | (0.33) | (0.51) | (0.59) | (0.49) | (0.45) | (0.60) |

Substance of the present invention administered group: Administration of the substance initiated after 4 days of implantation of tumor cells intraperitoneally.
Significantly difference for the control group *: $p < 0.05$, **: $p < 0.01$
S.E.: Standard error

Life-prolongation Effect in the Substance i.p. Administered Group

In the ascites control group, death was observed after 7 days of tumor inoculation (one animal, 1/5), one animal in day 8 (2/5) and one in day 10 (3/5). No death in the substance administered group was observed (on the day 10 after inoculation). Result is shown in Table 9.

TABLE 9

| \multicolumn{10}{c}{Days after tumor implantation} | | | | | | | | | |
|---|---|---|---|---|---|---|---|---|---|
| 1 | 2↓ | 3 | 4↓ | 5 | 6↓ | 7 | 8↓ | 9 | 10↓ |
| \multicolumn{10}{c}{Control (n = 5)} | | | | | | | | | |
| \multicolumn{10}{c}{Survival rates (%)} | | | | | | | | | |
| 100 | 100 | 100 | 100 | 100 | 100 | 80 | 60 | 60 | 40 |
| (5/5) | (5/5) | (5/5) | (5/5) | (5/5) | (5/5) | (4/5) | (3/5) | (3/5) | (2/5) |
| \multicolumn{10}{c}{Substance administered group (n = 6)} | | | | | | | | | |
| \multicolumn{10}{c}{Survival rates (%)} | | | | | | | | | |
| 100 | 100 | 100 | 100 | 100 | 100 | 100 | 100 | 100 | 100 |
| (6/6) | (6/6) | (6/6) | (6/6) | (6/6) | (6/6) | (6/6) | (6/6) | (6/6) | (6/6) |

↓: administration of the substance of the present invention

Organ and Tumor Weights of Tumor Bearing Mice

Organ weights (liver, kidneys, spleen and thymus) of mice of the ascites control group were decreased to 70–80% of the weight of organs compared to those of normal control group. Thymus weight was decreased 27%. In the substance administered group, increase in the weight of kidneys and spleen (121% and 142%), and significant decrease in the thymus (47%, $p<0.001$) was observed. Weights of ascites were 16.25 g in the ascites control group and 11.35 g in the substance administered group as shown in

TABLE 10

| | Liver (mg) | Kidneys (mg) | Spleen (mg) | Thymus (mg) | Ascites (mg) |
|---|---|---|---|---|---|
| \multicolumn{6}{c}{Control (n = 6)} | | | | | |
| Mean | 1982 | 529 | 166 | 55 | — |
| (S.E.) | (39) | (14) | (10) | (3) | (—) |
| \multicolumn{6}{c}{Control, ascites} | | | | | |
| Mean | 1588 | 370 | 130 | 15 | 16.25 |
| (S.E.) | (—) | (—) | (—) | (—) | (—) |
| \multicolumn{6}{c}{Substance administered group (n = 6)} | | | | | |
| Mean | 1747 | 641** | 236 | 26*** | 11.35 |
| (S.E.) | (166) | (27) | (30) | (3) | 2.75 |

Significant difference for the control group : $p < 0.01$, *: $p < 0.001$.
S.E.: Standard error Weights of liver, kidneys and spleen of the substance administered group in the solid tumor groups after 2 days of tumor inoculation were increased compared to normal control, and the thymus weight was slightly decreased. Weight of solid tumor in the substance administered in tumor group is 529±149 mg, which is significant difference ($p<0.05$) from the solid tumor control of 1564±396 mg. Weight of the substance i.p. administered group is 1005±384 mg. which shows decrease in weight without significant difference. Results are shown in Table 11.

TABLE 11

| | Liver (mg) | Kidney (mg) | Spleen (mg) | Thymus (mg) | Weight of tumor (mg) |
|---|---|---|---|---|---|
| \multicolumn{6}{c}{Control (n = 6)} | | | | | |
| Mean | 1982 | 529 | 166 | 55 | — |
| (S.E.) | (39) | (14) | (10) | (3) | (—) |
| \multicolumn{6}{c}{Control, solid tumor (n = 5)} | | | | | |
| Mean | 2434* | 597* | 284* | 47 | 1564* |
| (S.E.) | (153) | (22) | (38) | (4) | (397) |
| \multicolumn{6}{c}{Substance administered group, in the tumor (n = 6)} | | | | | |
| Mean | 2404* | 550 | 237* | 54 | 529* |
| (S.E.) | (132) | (27) | (24) | (3) | (149) |
| \multicolumn{6}{c}{Substance administered group, i.p. (n = 6)} | | | | | |
| Mean | 2332* | 540 | 273*** | 46* | 1005 |
| (S.E.) | (131) | (13) | (18) | (1) | (384) |

Substance administered group: Administration of the substance initiated after 2 days of tumor implantation.
Significant difference for the control group *: $p < 0.05$, ***: $p < 0.001$ In the substance administered in tumor and i.p. group, for which the substance as administered after 4 days of tumor inoculation, significant increase in liver and spleen weights was observed. Tumor weight was 1167±244 mg. Results are shown in Table 12.

TABLE 12

| | Liver (mg) | Kidneys (mg) | Spleen (mg) | Thymus (mg) | Weight of tumor (mg) |
|---|---|---|---|---|---|
| \multicolumn{6}{c}{Control (n = 6)} | | | | | |
| Mean | 1982 | 529 | 166 | 55 | — |
| (S.E.) | (39) | (14) | (10) | (3) | (—) |
| \multicolumn{6}{c}{Control, Solid tumor (n = 5)} | | | | | |
| Mean | 2434* | 597* | 284** | 47 | 1564 |

TABLE 12-continued

|  | Liver (mg) | Kidneys (mg) | Spleen (mg) | Thymus (mg) | Weight of tumor (mg) |
|---|---|---|---|---|---|
| (S.E.) | (153) | (22) | (38) | (4) | (397) |
| Substance administered group in the tumor/i.p. (n = 6) | | | | | |
| Mean | 2505*** | 513 | 358** | 49 | 1167 |
| (S.E.) | (107) | (18) | (29) | (1) | (244) |

Substance administered group: administration of the substance initiated after 4 days of tumor implantation.
Significant difference for the control group *: p < 0.05, : p < 0.01, *: p < 0.001.
S.E.: Standard error Safety Test of Consecutive Administration (10 Times for Every Other Days) of the Substance Obtained in Example 1

Body weight changes

Body weight changes of the normal mice with the substance administered every other days for 10 times were measured. No difference between the substance administered group and control was observed. In the control group, normal increase in body weight was observed. Decrease in mean body weight in the substance administered group compared to the control group was observed after 12 days (6th administration). Significant difference was observed in day 16 (8th administration, p<0.05), and this was continued to day 20 (10th administration). One animal was died after 8th administration (day 19). Result is shown in Table 13.

TABLE 13

|  | Days | | | | | |
|---|---|---|---|---|---|---|
|  | 0 | 2↓ | 4↓ | 6↓ | 8↓ | 10↓ |
| Control (physiological saline, i.p. n = 5) | | | | | | |
| Mean | 30.6 | 31.3 | 32.5 | 33.4 | 34.7 | 35.2 |
| (S.E.) g | (0.38) | (0.40) | (0.31) | (0.38) | (0.41) | (0.39) |
| Substance administered group (i.p., n = 6) | | | | | | |
| Mean | 30.9 | 31.2 | 33.0 | 34.2 | 34.8 | 35.4 |
| (S.E.) g | (0.66) | (0.52) | (0.63) | (0.75) | (0.38) | (0.49) |
|  | 12↓ | 14↓ | 16↓ | 18↓ | 20↓ | 22↓ |
| Control (physiological saline, i.p., n = 5) | | | | | | |
| Mean | 37.0 | 37.9 | 38.5 | 38.5 | 38.2 | 38.6 |
| (S.E.) g | (0.36) | (0.32) | (0.37) | (0.37) | (0.34) | (0.70) |
| Substance administered group (i.p., n = 6) (one animal dead on day 19) | | | | | | |
| Mean | 35.7 | 36.5 | 36.5* | 37.7 | 37.8 | 38.0 |
| (S.E.) g | (0.49) | (0.53) | (0.53) | (0.64) | (0.85) | (077) |

↓: Administration of the substance (number of administration: total 10)
Significant difference for the control *: p < 0.05
S.E.: Standard error Weight of liver. kidneys and thymus in both of the administered and the control groups were almost same levels. Weight of the spleen was significantly increased to 165% (p<0.01). Result is shown in Table 14.

TABLE 14

|  | Liver (mg) | Kidneys (mg) | Spleen (mg) | Thymus (mg) |
|---|---|---|---|---|
| Control (n = 5) | | | | |
| Mean | 2143 | 583 | 127 | 45 |
| (S.E.) | (73) | (16) | (11) | (7) |
| Substance administered group (n = 6) | | | | |
| Mean | 2308 | 532 | 210** | 44 |
| (S.E.) | (64) | (31) | (13) | (4) |

Substance administered group: Substance was administered on the every other days, total 10 days.
Significant difference for the control **: p < 0.01.
S.E.: Standard error.

Variations of leukocytes counts and erythrocyte count and hemoglobin weights were observed in leukocytes counts $10000/\mu l$ (control group) and $124000/\mu l$ (administered group). Erythrocyte count and hemoglobin weight were decreased, especially significant decrease in hemoglobin weight of 82% in the administered group compared to the control (p<0.05). Results are shown in Table 15.

TABLE 15

|  | No. of leukocytes ($\mu l$/ml) | No. of erythrocytes ($10^4$/ml) | hemoglobin (g./dl) |
|---|---|---|---|
| Control (n = 5) | | | |
| Mean | 10000 | 931 | 14.0 |
| (S.E.) | (1300) | (33.3) | (0.28) |
| Substance administered group (n = 6) | | | |
| Mean | 12400 | 829 | 11.5* |
| (S.E.) | (3130) | (51.6) | (0.79) |

Significant difference for the control *: p < 0.05.
S.E.: Standard error.

Result of antitumor effect of the substance obtained in Example 1 is summarized as follows.

Intraperitoneal administration of the substance in Sarcoma-180 ascites tumor bearing mice was confirmed by increased life prolongation and suppressive effect against ascites tumor. Intraperitoneally inoculated ascites tumor mice (control) dead on day 7 after inoculation. Survival rate on the day of the biopsy (day 11) is 40% with mean ascites weight of 16.25 g. No death was observed in the substance administered group. Lean ascites weight was 11.35±2.57 g. In the intraperitoneal cavity of the substance administered group, white aggregates, which seemed to be tumor cells, were observed. This was estimated to be a result of an effect of the substance.

Significant increase in erythrocyte counts and hemoglobin weight of the ascites control compared to the normal control were observed, which might be a deterioration of the symptom. In the hematological findings of the substance administered group, significant decrease compared to the normal control was observed. However, it showed almost normal value with slight good condition contrary to the ascites control. Decreased weight of the liver, kidneys, spleen and thymus (atrophy) in the ascites control compared to the normal control were observed. The substance administered group showed increased weights of kidneys and spleen, which indicated the homeostasis of the animals.

In Sarcoma-180 solid tumor inoculated in the right femoral region subcutaneously, no death was observed in the experimental groups. Tumor weight of the substance administered in tumor group was about 33%; the substance i.p. administered group was 64%; and the substance administered in tumor/i.p. group was 74%, compared to the solid tumor control group. Tumor regession below 0.4 g) was observed in the half number of the substance administered in tumor group. Significant decrease (p<0.05) in the mean tumor weight compared to solid tumor control was observed. In the solid tumor control, increase in leukocytes, decrease in erythrocyte (p<0.05) and hemoglobin (p<0.05) compared to the normal control were observed. No significant difference between the normal control and the substance administered in tumor group was observed and the value was almost equal level to the normal mice.

Safety of the Consecutive Administration of the Substance

The substance 1 mg was dissolved in physiological saline 10 ml. 0.2 ml thereof was administered intraperitoneally in mice on the every other days, total 10 times. No death was observed, except one died on day 19 (after 8th administration). Body weight decrease was observed after 12–20 days of administration compared to the normal control and was to be an effect of the substance. Increase in leukocytes counts and decrease in erythrocyte count without significant difference and significant decrease in hemoglobin (p<0.05) were observed in the substance administered group. From these symptoms, anemia was suspected. Significant increase in spleen weight was observed.

Above results indicate no problems on safety of the substance.

EXAMPLE 5

The substance 1 mg obtained in Example 1 was dissolved in 50 mM phosphate buffer, pH 7.2, 10 ml and was set to the original preparation. Keratinocytes (GK cells) and fibroblasts (GF cells) originated from human gingiva isoalted in Dept. of Preventive and Community Dentistry, School of Dentistry at Tokyo, The Dental University of Nippon were used. HeLa $S_3$ cells of human uterocervical cancer origin and HT-1080 cells of human lung cancer origin were also used. Cultivations of human gingival fibroblasts and cancer cells were performed in 10% bovine fital serum added Eagle's MEM and cultivation of keratinocytes was performed in serum-free medium for keratinocytes (SFM, Gibco), at 37° C. under 5%-$CO_2$-95% air with 100% humidity.

Aliquot of the original extract, in its 10-fold stepwise dilution with PBS (-), was added to the cell cultured liquid. Viability of the cells was made by Trypan blue. DNA synthesis of the cells was measured by after treatment of the cells with the extracts of various concentration for 3 hours, pulse-labelling the cells with 37 KBg/ml of $^3$H-thymidine, and radioactivities of acid insoluble fraction of the cells were measured.

DNA synthesis after treating with the cellular extracts is shown in Table 16. DNA syntesis was suppressed by the extracts dose-dependently. The suppression was observed higher in cancer cells than in adult gingival cells.

TABLE 16

| Concentration of the substance* | Uptake of $^3$H-tymidine (control %) | | | |
| --- | --- | --- | --- | --- |
| | GK cell | GF cell | HeLa $S_3$ cell | HT-1080 cell |
| $10^{-6}$ | 99 | 103 | 107 | 107 |
| $10^{-5}$ | 102 | 103 | 93 | 95 |
| $10^{-4}$ | 99 | 101 | 82 | 87 |
| $10^{-3}$ | 93 | 93 | 61 | 63 |
| $10^{-2}$ | 84 | 85 | 26 | 20 |
| $10^{-1}$ | 61 | 64 | 3 | 2 |

*Dilution rate of the original extraction

What is claimed is:

1. An isolated and purified Asn-linked glycoprotein having a molecular weight of 32–48 kDa, which absorbs to Con. A.

2. The glycoprotein according to claim 1, which has a molecular weight of 65±7 kDa.

3. The glycoprotein according to claim 1, which has a molecular weight of 58±6 kDa.

4. The glycoprotein according to claim 1, which has a molecular weight of 48±5 kDa.

5. The gycoprotein according to claim 1 which originates from an isolated and purified micoorganism belonging to genus Aspergillus.

6. The glycoprotein according to claim 5, wherein the microorganism belonging to genus Aspergillus is *Aspergillus Flavus*.

7. The glycoprotein according to claim 6, wherein the *Aspergillus Flavus* is *Aspergillus Flavus* SRT.

8. The gycoprotein according to claim 7, wherein the *Aspergillus Flavus* is *Aspergillus Flavus* SRT (FERM BP-5030).

9. The glycoprotein according to claim 1, which has antitumor activity.

10. An isolated and purified microorganism which is Aspergillus flavus SRT (FERM BP-5030).

11. A process for the production of Asn-linked gycoproteins having a molecular weight of 32–84 kDa, which adsorbs to Con. A, comprising culturing an isolated and purified microorganism which is *Aspergillus Flavus* SRT (FERM BP-5030) and isolating the thus-produced Asn-linked glycoprotein having a molecular weight of 32–84 kDa, which adsorbs to Con. A.

12. A process according to claim 11, wherein isolation of the glycoprotein is performed by treating said microorganism with enzyme and detergent or with sudden depression of osmotic pressure.

13. A process according to claim 12, wherein the enzyme is Novozyme.

14. A process according to claim 12, wherein the detergent is sodium dodecylsulfate.

15. Antitumor active agent which contains a microorganism which is Asperqillus flavus SRT (FERM BP-5030) which produces an Asn-linked glycoprotein having a molecular weight of 32–84 kDa, which adsorbs to Con. A, a cell lysate thereof, and a said Asn-linked glycoprotein as active ingredients.

* * * * *